(12) United States Patent
Shreepathi Bhat (10) Patent No.: US 11,139,801 B2
(45) Date of Patent: Oct. 5, 2021

(54) POWER-ON RESET CIRCUIT

(71) Applicant: TEXAS INSTRUMENTS INCORPORATED, Dallas, TX (US)

(72) Inventor: Avinash Shreepathi Bhat, Tucson, AZ (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

(21) Appl. No.: 17/034,157

(22) Filed: Sep. 28, 2020

(65) Prior Publication Data

US 2021/0013872 A1      Jan. 14, 2021

Related U.S. Application Data

(62) Division of application No. 16/278,575, filed on Feb. 18, 2019, now Pat. No. 10,790,806.

(51) Int. Cl.
| | | |
|---|---|---|
| *H03K 5/24* | (2006.01) | |
| *H03K 3/012* | (2006.01) | |
| *A61N 1/08* | (2006.01) | |
| *A61N 1/378* | (2006.01) | |
| *H03K 17/687* | (2006.01) | |
| *G06F 1/24* | (2006.01) | |
| *A61N 1/362* | (2006.01) | |

(52) U.S. Cl.
CPC .............. *H03K 3/012* (2013.01); *A61N 1/08* (2013.01); *A61N 1/378* (2013.01); *G06F 1/24* (2013.01); *H03K 5/24* (2013.01); *H03K 17/687* (2013.01); *A61N 1/362* (2013.01)

(58) Field of Classification Search
CPC .......... H03K 3/012; H03K 5/08; H03K 5/082; H03K 5/084; H03K 17/22; H03K 17/223; H03K 17/687; G06F 1/24
See application file for complete search history.

(56) References Cited

U.S. PATENT DOCUMENTS

| | | | |
|---|---|---|---|
| 10,790,806 B2* | 9/2020 | Shreepathi Bhat .. | H03K 17/687 |
| 2006/0164136 A1* | 7/2006 | Shin ...................... | H03K 17/223 327/143 |
| 2010/0109742 A1* | 5/2010 | Honda ............. | H03K 19/00384 327/333 |
| 2014/0266140 A1 | 9/2014 | Iriarte et al. | |
| 2014/0266314 A1 | 9/2014 | Iriarte et al. | |

* cited by examiner

*Primary Examiner* — Long Nguyen
(74) *Attorney, Agent, or Firm* — Michael A. Davis, Jr.; Charles A. Brill; Frank D. Cimino (57) ABSTRACT

A power-on reset (POR) circuit includes first, second and third resistors. A first transistor has a first control terminal and first and second voltage terminals. A second transistor has a second control terminal and third and fourth voltage terminals. A third transistor has a third control terminal and fifth and sixth voltage terminals. The first control terminal is coupled via the first resistor to the second voltage terminal. The third voltage terminal is coupled via the second resistor to the first voltage terminal. The second control terminal is coupled via the third resistor to the fourth voltage terminal. The third control terminal is coupled to the third voltage terminal. The fifth voltage terminal is coupled to the first control terminal. A voltage buffer is coupled to the fifth voltage terminal.

5 Claims, 5 Drawing Sheets

POWER-ON RESET CIRCUIT

CROSS-REFERENCE TO RELATED APPLICATION

This application is a divisional of U.S. patent application Ser. No. 16/278,575 filed Feb. 18, 2019, which is incorporated herein by reference.

SUMMARY

A power-on reset (POR) circuit includes first, second and third resistors. A first transistor has a first control terminal and first and second voltage terminals. A second transistor has a second control terminal and third and fourth voltage terminals. A third transistor has a third control terminal and fifth and sixth voltage terminals. The first control terminal is coupled via the first resistor to the second voltage terminal. The third voltage terminal is coupled via the second resistor to the first voltage terminal. The second control terminal is coupled via the third resistor to the fourth voltage terminal. The third control terminal is coupled to the third voltage terminal. The fifth voltage terminal is coupled to the first control terminal. A voltage buffer is coupled to the fifth voltage terminal.

DETAILED DESCRIPTION OF EXAMPLE EMBODIMENTS

Low-power electronic devices are increasingly in demand, particularly in the medical device, mobile phone, and automotive contexts. Accordingly, electronic devices are configured to function in various power modes, such as active and standby modes. An active mode is a mode in which the electronic device performs its primary specified function(s). For example, in the active mode, an artificial pacemaker performs its primary function of generating electrical impulses into cardiac tissue in the event of an arrhythmia. In contrast, the standby mode is a mode in which an electronic device remains powered on without performing its primary function, but still performs one or more functions in the background (referred to herein as embedded functions). For example, the artificial pacemaker includes a power-on reset (POR) circuit that continuously monitors a supply voltage of the battery supplying power to the pacemaker to detect malfunctions, such as a sudden drop in the supply voltage of the battery. Electronic devices can reduce their overall power consumption if they are designed to perform their embedded functions at low power (e.g., 100 nanowatts (nW)). For example, a low-power POR circuit can reduce the overall power consumption of the device that contains the POR circuit.

Some POR circuits include a reference circuit, which outputs a reference signal. The POR circuit compares this reference signal with the supply voltage and generates a digital signal based on the comparison. This digital signal can indicate the status of the battery powering the device containing the POR circuit. Different techniques can be used to design the reference circuit. One such technique includes generating a bandgap voltage reference signal by coupling bipolar junction transistors (BJTs) having opposite temperature characteristics. For example, a BJT producing a complementary-to-absolute-temperature (CTAT) voltage between its base and emitter can be coupled with a set of two differently-sized BJTs producing a proportional-to-absolute-temperature (PTAT) voltage. The PTAT voltage is obtained by subtracting the base-to-emitter voltages of the two differently sized BJTs. Another technique combines PTAT and CTAT currents (rather than voltages) to generate a temperature-independent output voltage reference signal. In some cases, reference circuits can also include field-effect-transistors (FETs) having different threshold voltages, which can be implemented by distinct gate doping or selective channel implantation.

The POR circuits implemented using the reference circuits described above consume unacceptably large amounts of power. Also, some POR circuits occupy a relatively large silicon area and are incapable of monitoring sub-1V (e.g., 1V or less) supply voltage levels. Moreover, POR circuits in automotive applications (e.g., telematics control modules) or POR circuits in medical applications (e.g., artificial pacemakers) should comply with strict temperature requirements. For example, some medical products are specified to comply with an industrial-grade temperature specification of −40° C. and +125° C., inclusive. The POR circuits implemented using the reference circuits described above fail to operate at extreme corner temperatures, e.g., −40° C. and +125° C. This failure to comply with the temperature specification is undesirable. Moreover, some of the reference circuits described above exhibit significant current variation (e.g., 1500% of the variation that may occur in manufacturing processes), so the functional integrity of such POR circuits is not resistant to process, voltage, and temperature (PVT) variations. For at least these reasons, POR circuits that consume low power, operate at sub-1V, and overcome the PVT issues described above are desirable.

Accordingly, described herein are various examples of POR circuits that implement a modified reference circuit to overcome the challenges described above. Implementing the modified reference circuits described herein allows POR circuits to operate beyond the industrial-grade temperature specification (e.g., −40° C. and +125° C., inclusive). In some examples, the POR circuits implementing the modified reference circuit can operate between −50° C. and +150° C., inclusive. Further, the POR circuits described herein consume ultra-low power (e.g., less than 100 nW at room temperature), and can be configured to monitor even sub-1V supply voltage levels while using less silicon area than some designs. To achieve these advantages, the modified reference circuit includes at least two transistors configured to function in a sub-threshold region—a region of operation where the gate-to-source voltage of the transistor is less than the threshold voltage of the transistor. In at least some examples, one of the two transistors acts as a constant current source producing a subthreshold current. The interaction of this subthreshold current with the other transistor generates a reference voltage at a node in the modified reference circuit, and this reference voltage is used by the POR circuit to monitor the supply voltage. If the supply voltage is below the reference voltage, the POR circuit generates a digital logic 1 signal indicating that the supply voltage is below the desired voltage. If the supply voltage is above the reference voltage, the POR circuit generates a digital logic 0 signal indicating that the supply voltage is above the desired voltage.

Figure 1:
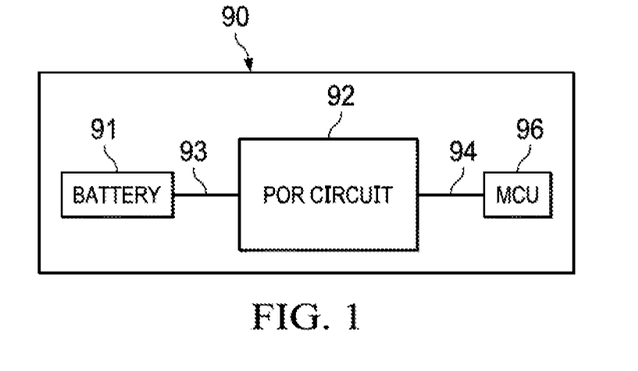
FIG. 1 depicts a system including a power-on reset (POR) circuit, in accordance with an example.

FIG. 1 depicts a block diagram of a system 90, which, in an example, is an electronic device, such as a medical device (e.g., artificial pacemaker) or a handheld communication device (e.g., a smartphone, a laptop computer, or a tablet). The system 90 comprises a battery 91 coupled to a POR circuit 92. The POR circuit 92 further couples to other circuits, e.g., a micro-controller unit (MCU) 96 via an output terminal 94. The example of FIG. 1 depicts the MCU 96 in system 90. However, in other examples, MCU 96 is an electrical unit separate from the system 90, and in such examples, the POR circuit 92 is configured to be coupled to MCU 96 (e.g., via a port in the system 90). The battery 91 is configured to provide power to the POR circuit 92 in any suitable manner. In some examples, the POR circuit 92 receives a voltage signal from the battery 91 via a connecting wire 93; monitors a magnitude of the voltage signal with a reference signal; and generates a logic output signal at the output terminal 94 based on a determination as to whether the magnitude of the voltage signal is above or below the reference signal. In some examples, if the logic output signal is high, the POR circuit 92 sends a reset (e.g., turn-off) signal to the MCU 96 indicating that a fault has occurred; and if the logic output signal is low, the POR circuit 92 permits the MCU 96 to continue operating without interruption. In one example, sending the reset signal turns off the MCU 96.

The following description includes examples of different modified reference circuit architectures, followed by a description of the POR circuit implementing these modified reference circuits. The specific technical advantages produced by these modified reference circuits—e.g., the ability to operate beyond industrial-grade temperature requirements, to consume low power, and to monitor supply voltages lower than 1V—are also described herein.

Figure 2A:
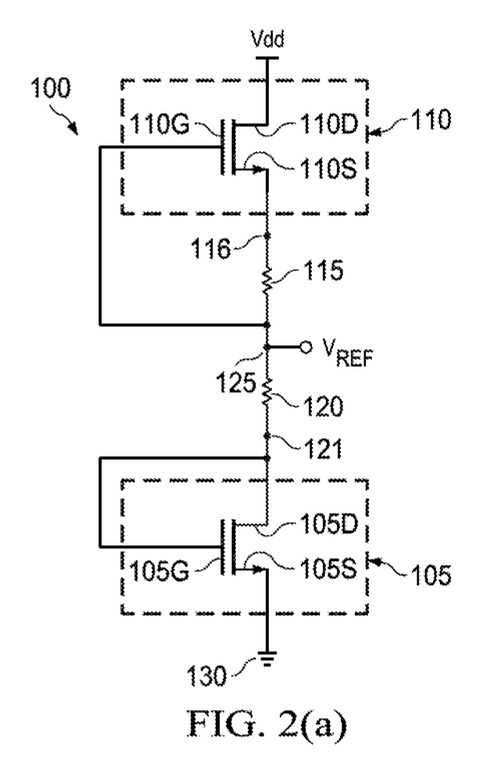
FIG. 2(a) depicts an illustrative modified reference circuit, in accordance with an example.

FIG. 2(a) depicts an illustrative modified reference circuit 100 in accordance with various examples. The modified reference circuit 100 assumes a 2-transistor, 2-resistor (2T-2R) architecture. The circuit 100 is a genericized depiction of various reference circuits that fall within the scope of this description. In some examples, the modified reference circuit 100 includes a transistor 110, a transistor 105, a resistor 115, and a resistor 120. The resistors 115, 120 have resistances R1, R2 respectively. The transistors 105, 110 depicted in FIG. 1 are metal-oxide-semiconductor-field-effect-transistors (MOSFETs). In one example, both the transistors 105, 110 are n-channel MOSFETs (nMOSFETs or NFETs). The transistor 110 comprises a drain terminal 110d, a source terminal 110s, and a gate terminal 110g. Similarly, the transistor 105 comprises a drain terminal 105d, a source terminal 105s, and a gate terminal 105g.

In some examples, the resistor 115 couples to the source terminal 110s at a node 116, and the resistor 115 also couples to a node 125; the gate terminal 110g couples to the node 125; and the drain terminal 110d couples to a voltage supply source Vdd. The battery 91 of FIG. 1 provides this voltage supply source Vdd to a POR circuit that implements the modified reference circuit 100. Consequently, the magnitude of this voltage supply source Vdd is monitored by the POR circuit described ahead in detail. In some examples, the resistor 120 couples to the drain terminal 105d at the node 121; the resistor 120 also couples to the node 125; the gate terminal 105g couples to the node 121; and the source terminal 105s couples to a ground source 130. A reference signal Vref—which is the output signal of the modified reference circuit 100—is produced at node 125.

In at least some examples, one of the two transistors, e.g., transistor 110, has a substantially zero (or near-zero) threshold voltage. As used herein, the substantially zero threshold voltage means that the transistor 110 is fabricated with an objective to achieve an absolute zero threshold voltage, but due to intrinsic process limitations and variations, the threshold voltage may lie within the range −0.1V to +0.1V, inclusive. Accordingly, from a microelectronics fabrication standpoint, due to intrinsic process limitations, achieving an absolute-zero threshold voltage is challenging, and thus a near-zero (e.g., 0.005V) threshold voltage for the transistor 110 is generally achieved. This near-zero threshold voltage, in this description, is considered to lie between the range of −0.1V to +0.1V, inclusive. In some examples, the transistor 110 is implemented using native MOSFETs, which are similar to a typical MOSFET, but it excludes the specially grown oxide layer of the typical MOSFET. The transistor 105 has a threshold voltage that is different than the threshold voltage of the transistor 110. In some examples, the transistor 105 is implemented using a standard MOSFET having a threshold voltage of 0.7 V-0.8 V. In other examples, the transistor 105 is implemented using a low threshold voltage MOSFET and has a low threshold voltage, for example, 0.5 V-0.6 V, inclusive.

As described above, the resistor 115 enables the transistor 110 to operate in the subthreshold region in that the resistor 115 acts as a degenerative resistor and provides a negative feedback to the gate terminal 110g, which enables the transistor 110 to function in a weak-inversion or the subthreshold region. The transistor 110 functioning in the subthreshold region means that the gate-to-source voltage supplied between the gate terminal 110g and the source terminal 110s is always less than the threshold voltage of the transistor 110. The transistor 110 functioning in the subthreshold region generates a sub-threshold current, meaning that when connected with Vdd at the drain terminal 110d, the transistor 110 generates a sub-threshold current $I_{STH}$. This sub-threshold current increases exponentially as the gate to source voltage increases. The sub-threshold current $I_{STH}$ can be modeled using equation 1:

$$I_{STH} = \mu C_{ox} \frac{W}{L}(m-1)V_T^2 \exp\left(\frac{V_{gs}-V_{th}}{mV_T}\right)\left(1-\exp\left(\frac{-V_{ds}}{V_T}\right)\right) \quad (1)$$

where μ is mobility, $C_{ox}$ is oxide capacitance, W is transistor width, L is transistor length, m is subthreshold slope factor (m=1+$C_d/C_{ox}$, where $C_d$ is depletion capacitance), $V_T$ is thermal voltage, $V_{gs}$ is gate-to-source voltage, $V_{th}$ is transistor threshold voltage, and $V_{ds}$ is drain-to-source voltage. The term $$\left(1-\exp\left(\frac{-V_{ds}}{V_T}\right)\right)$$

in equation 1 can be approximated to be equal to 1 if $V_{ds}>4V_T$. Thus, the subthreshold current $I_{110}$ can be approximated to equal to equation 2:

$$I_{110} = \mu C_{ox} \frac{W}{L}(m-1)V_T^2 \exp\left(\frac{V_{gs} - V_{th}}{mV_T}\right) \quad (2)$$

Using Ohm's law, Vgs can be equated to $(-I_{110} \times R1)$, and, because $\mu$, $C_{ox}$, W, L, and m are specific to the transistor 110, equation 2 can be rewritten as equation 3:

$$I_{110} = \beta_{110}(m_{110} - 1)V_T^2 \exp\left(\frac{-I_{110}R_1 - V_{th\_110}}{m_{110}V_T}\right) \quad (3)$$

where $\beta_{110}$ is equal to $$\mu * C_{ox} * \frac{W}{L}$$

of the transistor 110, $m_{110}$ is the subthreshold slope factor of the transistor 110, and $V_{th\_110}$ is the threshold voltage of the transistor 110. Using the resistor 115 brings about the term $I_{110}R_1$ in the exponential function of equation 3. Because the term $I_{110}R_1$ is proportional to temperature, it offsets the complementary-to-temperature change that occurs due to the term $V_{th\_110}$. Thus, the $I_{110}R_1$ term enables the reference circuit to operate between (and beyond) the needed industrial-grade temperature requirement of −40° C. and +125° C., inclusive, as the current $I_{110}$ doesn't vary exponentially at corner temperatures.

In some examples, $I_{STH}$ is in the range of 10-100 nA. The transistor 105, which may be a diode-connected transistor and which is biased to function in the sub-threshold region, receives this sub-threshold current $I_{STH}$ via resistor 120. Thus, the subthreshold current flowing in the transistor 105 can be modeled by using equation 2 as equation 4:

$$I_{105} = \beta_{105}(m_{105} - 1)V_T^2 \exp\left(\frac{V_{gs\_105} - V_{th\_105}}{m_{105}V_T}\right) \quad (4)$$

where $\beta_{105}$ is equal to $$\mu * C_{ox} * \frac{W}{L}$$

of the transistor 105, $m_{105}$ is subthreshold slope factor of the transistor 105, and $V_{th\_105}$ is the threshold voltage of the transistor 105. Because the same current flows in both the transistors 105, 110, the equations of the currents $I_{105}$ and $I_{110}$ are equated to obtain an analytical solution (see equation (5)) for Vref.

$$V_{ref} = V_{th\_105} - k * V_{th\_110} + m_{105}V_T \ln\left(\frac{(m_{110} - 1)\beta_{110}}{(m_{105} - 1)\beta_{105}}\right) \quad (5)$$

where $$R_2 = k * R_1 = \frac{m_{105}}{m_{110}} * R_1$$

Equation 5 can be decomposed into first and second components, where the first component includes $(V_{th\_105} - k*V_{th\_110})$ and the second component includes $$\left(m_{105}V_T \ln\left(\frac{(m_{110} - 1)\beta_{110}}{(m_{105} - 1)\beta_{105}}\right)\right).$$

Both the first and second components are either proportional or complementary to absolute temperature. Alternatively, both the first and second components are proportional and complementary to absolute temperature. In either case, Vref can be temperature insensitive. Accordingly, in the first component, threshold voltages are complementary to absolute temperature and "k" is proportional to absolute temperature, and the second component is a function of widths and lengths of the two transistors 105, 110. Thus, by selecting the resistances R1, R2 and the widths and lengths of the transistors 105, 110 appropriately, the temperature dependences of the two components cancel each other, which enables the circuit to operate between (and beyond) the needed industrial-grade temperature requirement of −40° C. and +125° C., inclusive. Also, because both the transistors 110 and 105 are NFETs, they are substantially insensitive to process variations. The modified reference circuit 100 consumes ultra-low currents as low as 20 nA because the transistors 105, 110 function in the sub-threshold region.

As the supply voltage Vdd increases from 0 V, the reference voltage Vref increases with an increasing Vdd. However, the magnitude to which the reference voltage Vref can increase, as indicated by equation 5, is a function of the threshold voltages of the transistors 105, 110.

The subthreshold slope factor (m) is substantially constant for a given transistor (and is usually substantially equal to 1). By approximating the slope factors of both the transistors 105, 110 to be equal, the modified reference circuit 100 assumes a 2-transistor, 1-resistor (2T-1R) architecture further depicted in FIG. 2(b).

Figure 2B:
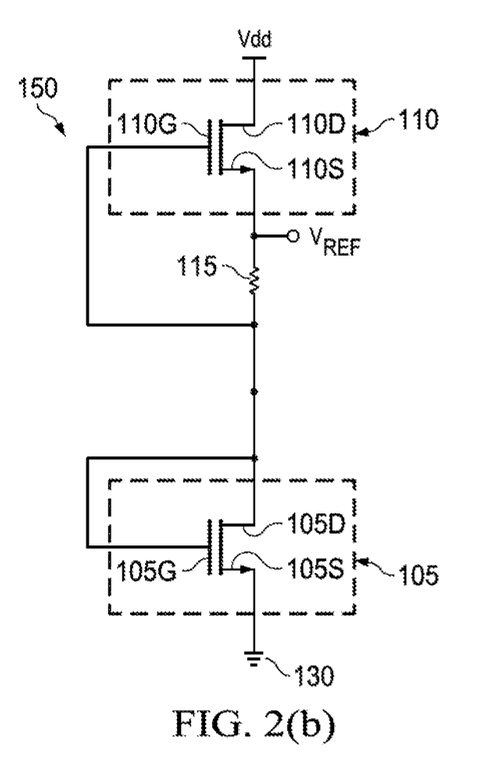
FIG. 2(b) depicts another illustrative modified reference circuit, in accordance with an example.

FIG. 2(b) shows an illustrative modified reference circuit 150 in accordance with various examples. The modified reference circuit 150 implements the 2-transistor 1-resistor (2T-1R) architecture. The modified reference circuit 150 is similar to the reference circuit 100, except that the subthreshold slope factors of the transistors 105, 110 are approximated to be equal, which enables the transformation of the 2T-2R architecture into the 2T-1R architecture (with resistor 120 removed). In other words, the transistors 105, 110 can be fabricated such that the subthreshold slope factors of the transistors 105, 110 are approximated to be equal. Furthermore, the description of the modified reference circuit 100 applies to the modified reference circuit 150, except that the resistor 120 of FIG. 2(a) is shorted (or is made to be zero); the value of k in the equation 5 is equal to 1, and the constant voltage reference signal is produced at the source terminal 110s instead of the node 125. In effect, the Vref generated by the modified reference circuit 150 can be modeled using equation 6:

$$V_{ref} \approx V_{th\_105} - k * V_{th\_110} + m_{105}V_T \ln\left(\frac{(m_{110} - 1)\beta_{110}}{(m_{105} - 1)\beta_{105}}\right) \quad (6)$$

Similar to equation 5, equation 6 can also be broken down into first and second components, where the first component includes $(V_{th\_105} - V_{th\_110})$ and the second component includes $$\left(m_{105}V_T \ln\left(\frac{(m_{110} - 1)\beta_{110}}{(m_{105} - 1)\beta_{105}}\right)\right).$$

Similar to equation 5, both the first and second components of equation 6 are either proportional or complementary to absolute temperature, and this enables Vref to function in between (and beyond) the needed industrial-grade temperature requirement of −40° C. and +125° C., inclusive. Also, because both the transistors 110 and 105 are NFETs, they are insensitive to process variations.

This description includes examples of genericized architectures of the modified reference circuits. Examples of POR circuits implementing different modified reference circuits are described herein.

Figure 3A:
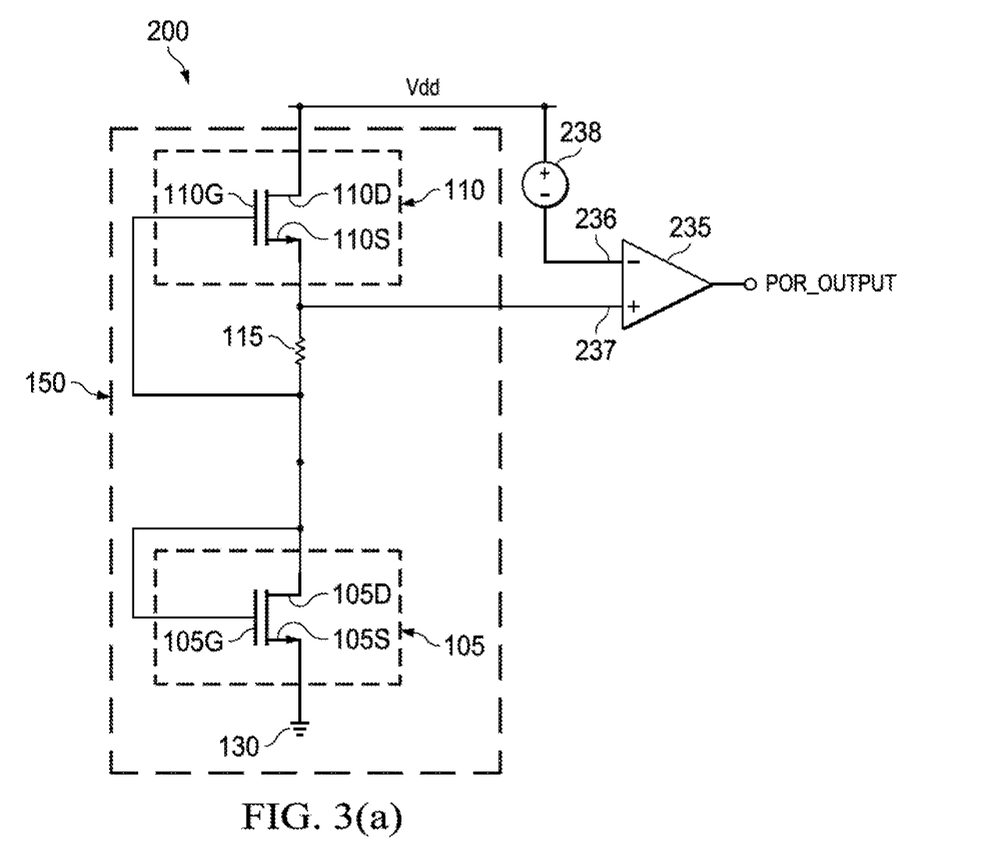
FIG. 3(a) depicts a schematic diagram of an illustrative POR circuit, in accordance with an example.

FIG. 3(a) shows a schematic diagram of an illustrative POR circuit 200. The POR circuit 200 is a genericized depiction of various POR circuits that fall within the scope of this description. The POR circuit 200 includes the modified reference circuit 150, described above in FIG. 2(b). The description of the modified reference circuit 150 provided above applies here in the description of the POR circuit 200. In at least some examples, the POR circuit 200 also includes a comparator 235 having first and second terminals 236, 237, respectively. The comparator 235 is configured to compare the reference voltage Vref and the supply voltage Vdd. In some examples, the first terminal 236 couples to the voltage source Vdd via an offset voltage source 238 and the second terminal 237 couples to the source terminal 110s. In some examples, the offset voltage 238 can be used to offset a voltage headroom, which, in this example, is the minimum drain-to-source headroom voltage needed for the subthreshold current $I_{STH}$ to flow. The offset voltage 238 can be required as the absence of such offset voltage 238 does not allow for the comparator to trip from one logic level to another. For example, without the offset voltage 238, the magnitude of the voltage source Vdd would have been higher than the reference voltage Vref, and the comparator 235 would output a logic low signal. In some examples, the offset voltage 238 is coupled between the first terminal 236 and the supply voltage Vdd.

In some examples, the POR circuit 200 includes a bias circuit that provides a bias current of the comparator 235. In some examples, a portion of the modified reference circuit 150, e.g., the transistor 105 forms the bias circuit. In some examples, the bias circuit is implemented using a current mirror circuit (not expressly shown in FIG. 3(a)).

For simplicity, in this description of the POR circuit 200 operation, the modified reference circuit 150 uses a minimum headroom voltage of 50 mV, the offset voltage 238 introduces a 70-mV voltage offset, the supply voltage Vdd is being turned on for the first time, this supply voltage Vdd increases to 0.8V and then stabilizes at 0.8V supply voltage, and the threshold voltages and the design constraints (e.g., length, width) of the transistors 110, 105 are selected to limit the reference voltage Vref to 0.7 V. Accordingly, the Vref does not increase beyond 0.7 V, because suitably selected threshold voltage and lengths and widths of the transistor 110, 105 limit the reference voltage Vref to 0.7 V.

Still referring to the operation of the POR circuit 200, the voltage at the drain terminal 110d increases as the supply voltage Vdd is turned on. After increasing to 50 mV (the headroom voltage), the subthreshold current $I_{STH}$ starts flowing, and the source terminal 110s starts outputting the reference voltage Vref. The reference voltage Vref increases as the supply voltage Vdd increases. As the supply voltage Vdd increases to, for example, 0.4V, the reference voltage Vref increases to 0.35V (e.g., 0.4V minus the headroom voltage). At this point, the first terminal 236 receives a 0.33V signal, which is lower than the reference voltage Vref. Thus the comparator 235 outputs logic high 1 and indicates that the supply voltage Vdd is lower than the reference voltage Vref. As the voltage supply increases to 0.78V, the reference voltage limits itself to 0.70V, and the first terminal 236 receives a 0.71V signal. This scenario makes the reference voltage Vref lower than the signal received at the first terminal 236, so the digital signal POR_OUTPUT trips from logic high 1 to logic low 0, indicating that the supply voltage Vdd is higher than the reference voltage. The supply voltage Vdd further increases to 0.8 V before stabilizing at that voltage level. The POR circuit 200 monitors the supply voltage Vdd (which is 0.8V) and continuously monitors to determine whether the supply voltage Vdd is above or below the reference voltage Vref. During a fault, the magnitude of the voltage supply Vdd dips below the reference voltage 0.7V, and, in such a scenario, the comparator 235 outputs a logic 1 and indicates to turn off the circuits coupled to the POR circuit 200.

It can be determined from the operation of the POR circuit 200 that the circuit trips from logic high 1 to logic low 0 indicating that the supply voltage Vdd is higher than the reference voltage at the following $V_{TRIP}$ voltage. This voltage can be computed by equation 7:

$$V_{TRIP+} \cong V_{th\_105} V_{th\_110} + V_{238} + mV_T \ln\left(\frac{\beta_{110}}{\beta_{105}}\right) \quad (7)$$

where $\beta_{105}$ and $\beta_{110}$ are equal to $$\mu * C_{ox} * \frac{W}{L}$$

of the transistors 105, 110, respectively; m is subthreshold slope factor of both the transistors 105, 110, $V_{th\_105}$ is the threshold voltage of the transistor 105, and $V_{th\_110}$ is the threshold voltage of the transistor 110.

Figure 3B:
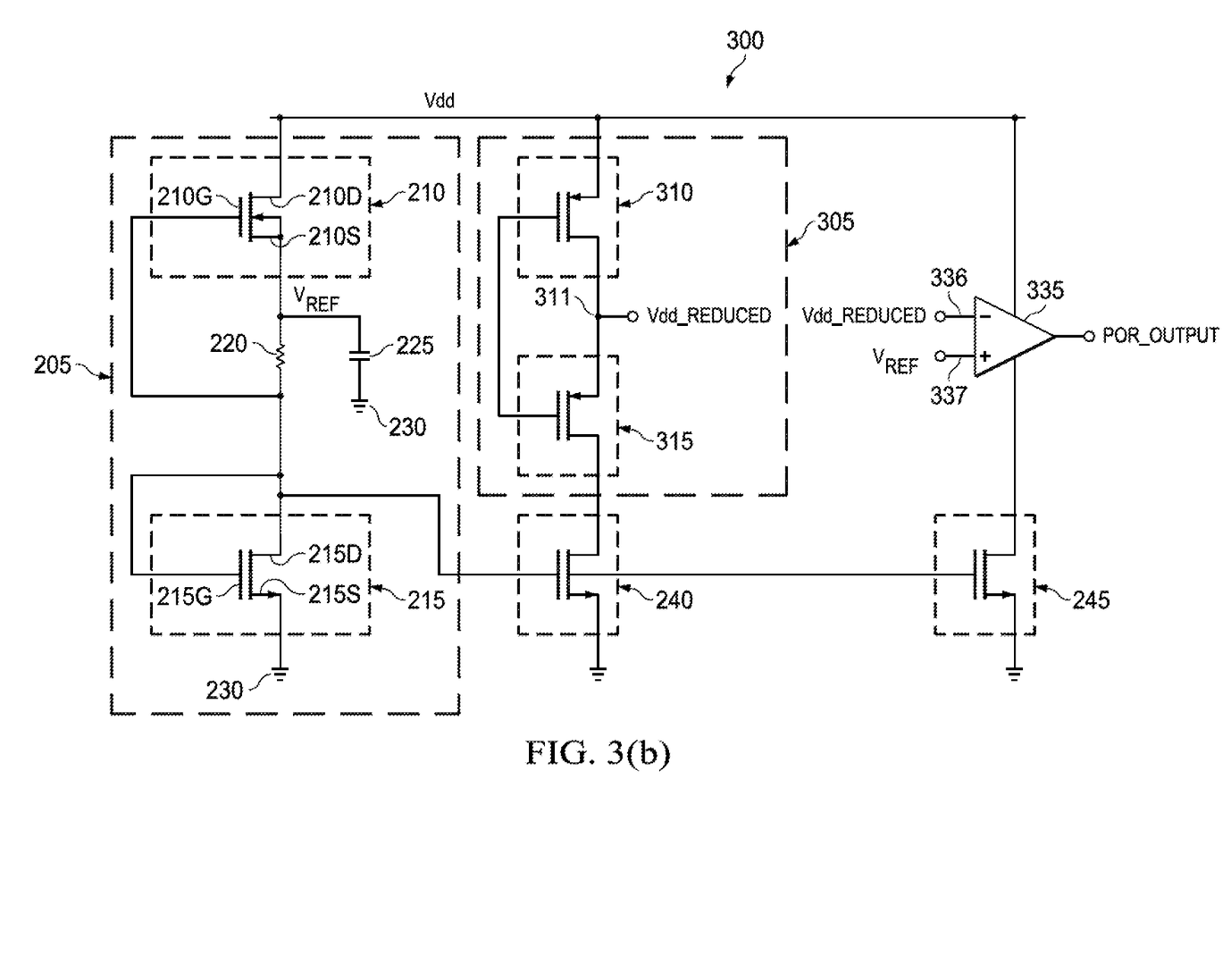
FIG. 3(b) depicts a schematic diagram of another illustrative POR circuit, in accordance with an example.

In some examples, the voltage source 238 is implemented by one or more transistors. One such implementation is described in FIG. 3(b), which is a schematic diagram of another illustrative POR circuit 300. FIG. 3(b) also depicts the bias circuitry that is used to provide bias current to the comparator 235. The POR circuit 300 includes a modified reference circuit 205 that assumes the 2T-1R architecture described in FIG. 2(b). The modified reference circuit 205 is similar to the modified reference circuit 150 of FIG. 2(b) and the description of the modified reference circuit 150 applies to the modified reference circuit 205. Accordingly, the transistor 210 of the modified reference circuit 205 is similar to the transistor 110; the transistor 215 of the modified reference circuit 205 is similar to the transistor 105; and the resistor 115 is similar to the resistor 230 of the modified reference circuit 205. The connections in the modified reference circuit 205 are similar to the connections inside the modified reference circuit 150.

The modified reference circuit 205 includes a transistor 210 that couples to a voltage source Vdd via a drain terminal 210d, which is herein also referred to as a non-control terminal of the transistor 210. A gate terminal 210g of the transistor 210, which is also referred to herein as a control terminal, couples to a source terminal 210s of the transistor 210 via a resistor 220. The source terminal 210s is also referred to as a non-control terminal of the transistor 210. The modified reference circuit 205 further includes a transistor 215 coupled to the resistor 220. A gate terminal 215g, also herein referred to as a control terminal, of the transistor 215 is coupled to a drain terminal 215d of the transistor 215. The drain terminal 215d is herein referred to as a non-control terminal. In some examples, the source terminal 215s is coupled to the ground source 230. In some examples, the modified reference circuit 205 includes a capacitor 225 that couples to the source terminal 210s and a ground source 230. The capacitor 225 filters out the noise and provides immunity to supply voltage transients.

The POR circuit 300 further includes an offset circuit 305 that introduces an offset voltage (similar to the offset voltage 238 of FIG. 3(a)) in the POR circuit 300. In some examples, POR circuit 300 includes a comparator 335, which is similar to the comparator 235 of FIG. 3(a). The comparator 335 has first and second terminals 336, 337, respectively. The first terminal 336 receives a voltage signal—referred to as Vdd_reduced—that is Vdd reduced by a magnitude of the offset voltage introduced by the offset circuit 305 and the second terminal 337 receives a reference voltage Vref generated at the source terminal 210s. The POR circuit 300 includes a bias circuit formed by transistors 215, 240, and 245. The transistors 240, 245 couple to the drain terminal 215d to form current mirrors that provide bias current to the offset circuit 305 and the comparator 235, respectively. In some examples, the bias circuit includes a peaking resistor at the drain terminal 215d. The peaking resistor is useful to reduce the process and temperature variations in the currents conducted by the transistors 240 and 245.

In some examples, the offset circuit 305 includes self-cascoded transistors, such as transistors 310, 315. In such examples, the drain terminal of the transistor 310 couples to the source terminal of the transistor 315 at a node 311. The source terminal of the transistor 310 couples to the supply voltage Vdd. The gate terminals of the transistors 310, 315 couple to the drain terminal of the transistor 315, which further couples to the transistor 240. In the offset circuit 305 shown in FIG. 3(b), an offset voltage $\Delta V_{GS}$ that is the difference between the gate-to-source voltages of the transistors 310, 315 is generated between the node 311 and the supply voltage Vdd. Thus, the voltage signal Vdd_reduced is produced at the node 311. When a subthreshold current $I_{STH}$ flows in the modified reference circuit 205, because the transistors 240, 245 form current mirrors, the similar subthreshold current $I_{STH}$ flows in the offset circuit 305 and generates the voltage signal Vdd_reduced. The offset voltage can be calculated using equation 8:

$$\Delta V_{GS} = V_{GS\_310} - V_{GS\_315} = V_{th\_310} - V_{th\_315} + mV_T \ln\left(\frac{\beta_{210}}{\beta_{215}}\right) \quad (8)$$

where $V_{th\_310}$ is the threshold voltage of the transistor 310, $V_{th\_315}$ is the threshold voltage of the transistor 315, m is the subthreshold slope factor of the transistors 310, 315 (which, in one example, are equal), $V_T$ is the thermal voltage, $\beta 310$ is $$\mu_{310} * C_{ox\_310} * \frac{W\_310}{L\_310}$$

(where $\mu_{310}$ is mobility, $C_{ox\_310}$ is oxide capacitance, W_310 is transistor width, L_310 is transistor length of the transistor 310), and $\beta 315$ is $$\mu_{315} * C_{ox\_315} * \frac{W\_315}{L\_315}$$

(where $\mu_{315}$ is mobility of the transistor 315, $C_{ox\_315}$ is oxide capacitance of the transistor 315, W_315 is the transistor width of the transistor 315, and L_315 is the transistor length of the transistor 315). As indicated by equation 8, the offset voltage $\Delta V_{GS}$ can be made insensitive to temperature changes by selecting appropriate different threshold voltages, widths, and lengths of the transistors 310, 315. The transistors 310, 315 are shown to be p-type MOSFETs. However, in other examples, the transistors 310, 315 may be implemented using n-type MOSFETs, and in such examples, the coupling between the transistors 310, 315 may be adapted accordingly. In other examples, other circuits that can introduce an offset voltage can be employed.

In the POR circuit 300 operation, similar to the POR circuit 200 operation, the modified reference circuit 205 uses a 50 mV headroom voltage, the offset voltage $\Delta V_{GS}$ is equal to 70 mV, the supply voltage Vdd is being turned on for the first time, this supply voltage Vdd increases to 0.8V and then stabilizes at 0.8V supply voltage, and the threshold voltages and the design constraints (e.g., length, width) of the transistors 210, 215 are selected to limit the reference voltage Vref to 0.7 V, so the Vref does not increase beyond 0.7 V.

The voltage at the drain terminal 210d increases as the supply voltage Vdd is turned on. After increasing to 50 mV (the headroom voltage), the subthreshold current $I_{STH}$ starts flowing, and the source terminal 210s starts outputting the reference voltage Vref. The same subthreshold current $I_{STH}$ also flows in the offset circuit 305 and generates a Vdd_reduced signal at node 311. The subthreshold current $I_{STH}$ acts as a bias current for the comparator 335. Further, the reference voltage Vref increases as the supply voltage Vdd increases. As the supply voltage Vdd increases to, for example, 0.4V, the reference voltage Vref increases to 0.35V (e.g., 0.4V minus the headroom voltage) and the voltage signal Vdd_reduced increases to 0.33V. At this point, the first terminal 336 receives a 0.33V signal, which is lower than the reference voltage Vref. Thus, the comparator 335 outputs logic high 1 and indicates that the supply voltage Vdd is lower than the reference voltage Vref.

As the voltage supply increases to 0.78V, the reference voltage limits itself to 0.70V, and the first terminal 336 receives a 0.71V signal. This scenario makes the reference voltage Vref lower than the signal received at the first terminal 336, and thus the digital signal POR_OUTPUT of the comparator 335 trips from logic high 1 to logic low 0. This indicates that the supply voltage Vdd is higher than the reference voltage. The supply voltage Vdd may further increase to 0.8 V before stabilizing at that voltage level. The POR circuit 300 monitors the supply voltage Vdd (which is at 0.8V) and continuously monitors whether the supply voltage Vdd is above or below the reference voltage Vref. During a fault, the magnitude of the voltage supply Vdd may dip below the reference voltage 0.7V, and, in such a scenario, the comparator 335 outputs a logic 1 and indicates to turn off the circuits coupled to the POR circuit 300.

Similar to the POR circuit 200, a trip voltage ($V_{TRIP+}$) for the POR circuit 300 is computed by equation 9:

$$V_{TRIP+} \cong V_{th\_215} - V_{th\_210} + V_{th\_310} - V_{th\_315} + mV_T \ln\left(\frac{\beta_{210}\beta_{315}}{\beta_{215}\beta_{310}}\right) \quad (9)$$

where $\beta_{210}$, $\beta_{215}$, $\beta_{310}$, and $\beta_{315}$ are equal to $$\mu * C_{ox} * \frac{W}{L}$$

of the transistors 210, 215, 310, and 315, respectively; slope factors of transistors 210, 215, 310, and 315 are approximated to be equal to m; $V_{th\_215}$ is the threshold voltage of the transistor 215; $V_{th\_210}$ is the threshold voltage of the transistor 210; $V_{th\_310}$ is the threshold voltage of the transistor 310; and $V_{th\_315}$ is the threshold voltage of the transistor 315.

Figure 4A:
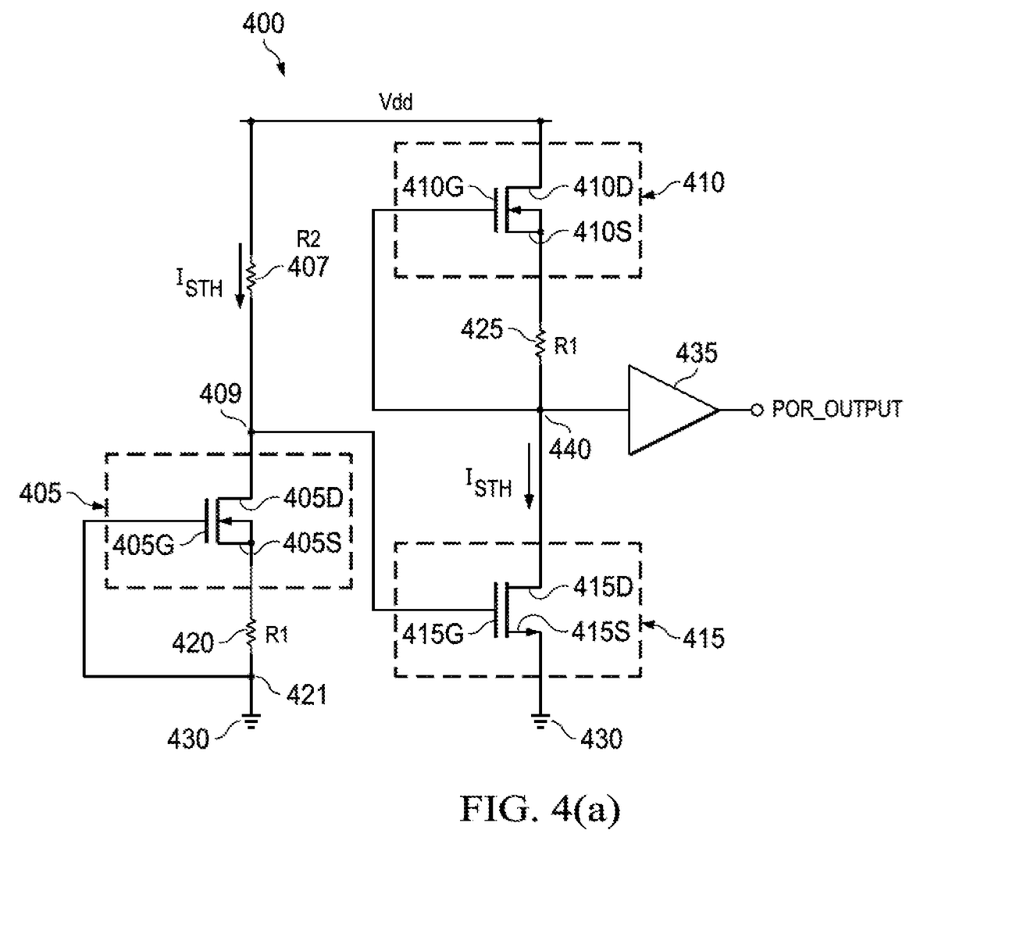
FIG. 4(a) depicts a schematic diagram of another illustrative POR circuit, in accordance with an example.

FIG. 4(a) shows POR circuit 400 implementing 2T-2R architecture. The POR circuit 400 includes a transistor 410 having a source terminal 410s, a drain terminal 410d, and a gate terminal 410g. The transistor 410 is coupled to a voltage source Vdd via the drain terminal 410d. The gate terminal 410g, which is also referred to as a control terminal of the transistor 410, is coupled to the source terminal 410s via a resistor 425 at a node 440. The source terminal 410s is also referred to as a non-control terminal of the transistor 410. The POR circuit 400 further includes a transistor 405 having a source terminal 405s, a drain terminal 405d, and a gate terminal 405g. The transistor 405 is coupled to the voltage source Vdd through the drain terminal 405d and via a resistor 407. The drain terminal 405d couples to the resistor 407 at a node 409. The gate terminal 405g (which is also referred to as a control terminal of the transistor 405) is coupled to the source terminal of the transistor 405 (also referred to as a non-control terminal of the transistor 405) via a resistor 420 at a node 421. The node 421 couples to a ground source 430. The POR circuit 400 further includes a transistor 415 having a gate terminal 415g, a drain terminal 415d, and a source terminal 415s. The gate terminal 415g (which is also referred to as a control terminal of the transistor 415) is coupled to the resistor 407. The drain terminal 415d (which is also referred to as a non-control terminal of the transistor 415) is coupled to the resistor 425 at node 440. The source terminal 415s couples to the ground source 430. The POR circuit 400 also includes a voltage buffer 435 (which is a buffer amplifier) that is coupled to the node 440 and outputs a POR_OUTPUT digital signal. The buffer 435, in one example, is implemented using standard threshold voltage devices, e.g., standard MOSFETs with threshold voltage equaling 0.7V.

In some examples, the transistors 405, 410 are native transistors that are biased using the degenerative resistors 420, 425, respectively, such that the transistors 405, 410 function in the subthreshold region. In such examples, the transistor 415 may be a standard transistor with a threshold voltage between 0.7 V-0.8 V or transistor with a low threshold voltage between 0.5 V-0.6 V. In some examples, the resistors 420, 425 have substantially well-matched resistances (e.g., resistances with +/−10 percent value of each other).

As described above, the POR circuit 400 is implemented using the 2T-2R architecture described in FIG. 2(a), and the 2T-2R architecture may not be readily visible in the POR circuit 400. However, the 2T-2R architecture of FIG. 2(a) may become apparent with the description of the POR circuit 400. For understanding's sake, the description of the POR circuit 400 may sometimes refer back to the modified reference circuit 100 of FIG. 2(a).

As described above, the resistors 420 and 425 have substantially equal resistances and are similar to the resistor 115 of circuit 100. The resistor 407 is similar to the resistor 120 of circuit 100. The transistors 405 and 410 are substantially similar and are native transistors and the description of the transistor 110 of FIG. 2(a) applies to the transistors 405, 410. The transistor 415 is analogous to the transistor 105 of FIG. 2(a). In the modified reference circuit 400, the voltage at the node 409 is equal to the difference of the supply voltage Vdd and the voltage drop across the resistor 407 ($V_{409}$=Vdd−($I_{STH}$*R2)). The voltage at node 409 acts as the gate-to-source voltage of the transistor 415.

As the supply voltage Vdd increases from zero to some finite value, e.g., 0.3V, a current $I_{STH}$ starts flowing due to the transistor 405. The current $I_{STH}$ flows into the resistor R2. At this point, the voltage at the node 409 starts increasing from zero to a voltage equaling 0.3−($I_{STH}$*R2). Because the voltage on the node 409 is less than the threshold voltage of the transistor 415 (which, in this example is 0.7V), the transistor 415 remains in an OFF state. At this point, the voltage at node 440 equals the supply voltage Vdd, and the voltage at the POR output is a logic high (e.g., 1) indicating that the supply voltage has not reached the desired voltage level (which, in this example is the sum of the threshold voltage of transistor 415 and voltage drop across R2). When the supply voltage Vdd approaches a voltage value equaling the sum of the threshold voltage of the transistor 415 and voltage drop across resistor R2, the transistor 415 begins to turn ON. This forces the voltage at the node 440 to fall below the supply voltage Vdd. When the supply voltage Vdd crosses a voltage value equaling the sum of the threshold voltage of the transistor 415 and voltage drop across resistor R2, the transistor 415 turns ON, which, in turn, forces the voltage on node 440 to be at a low voltage (e.g., 10 mV). At this point, the transistor 415 operates in a deep triode region, and due to near zero voltage at the node 440, the voltage at POR output becomes logic low. This signifies that the supply voltage has reached the desired level.

Similar to the POR circuits 200, 300, a trip voltage ($V_{TRIP+}$) for the POR circuit 400 is computed by equation 10:

$$V_{TRIP+} \cong V_{th\_415} - V_{th\_410} + mV_T \ln\left(\frac{\beta_{410}}{\beta_{415}}\right) \qquad (10)$$

where $\beta_{410}$ and $\beta_{415}$ are equal to $$\mu * C_{ox} * \frac{W}{L}$$

of the transistors 410, 415, respectively; m is a subthreshold slope factor of both the transistors 410, 415; $V_{th\_415}$ is the threshold voltage of the transistor 415; and $V_{th\_410}$ is the threshold voltage of the transistor 410.

By comparing equations 7, 10, the circuit 400 does not use the offset voltage source. Further, according to equations 7, 9 and 10, the trip voltage of the POR circuit is a function of the threshold voltage of at least some of the transistors in their respective POR circuits. In effect, the trip voltage can be altered based on the application. For example, if an application calls for the trip voltage to be less than 1V, POR circuits 200, 300 may be used. However, if an application calls for the trip voltage to be higher than 1V, e.g., 1.4 V, the threshold voltages of the transistors may be selected to make the trip voltage substantially equal to the desired trip voltage of 1.4 V.

Accordingly, in some examples, the trip voltage can be altered by adding additional transistors in a POR circuit. For example, based on the instant configuration of the POR circuit 400 (e.g., threshold voltages of the transistors used in the configuration shown in FIG. 4(*a*)), the trip voltage of the POR circuit 400 is limited to 850 mV +/−50 mV. By adding an additional transistor and a corresponding resistor, the trip voltage of the new circuit may be altered. An example of such a configuration is depicted in FIG. 4(*b*), which is an illustrative POR circuit 450 with an additional transistor and resistor, and based on the configuration of the POR circuit 450 (e.g., threshold voltages of the transistors used in the configuration shown in FIG. 4(*b*)), the trip voltage increases and limits at 1.43 V +/−75 mV.

Figure 4B:
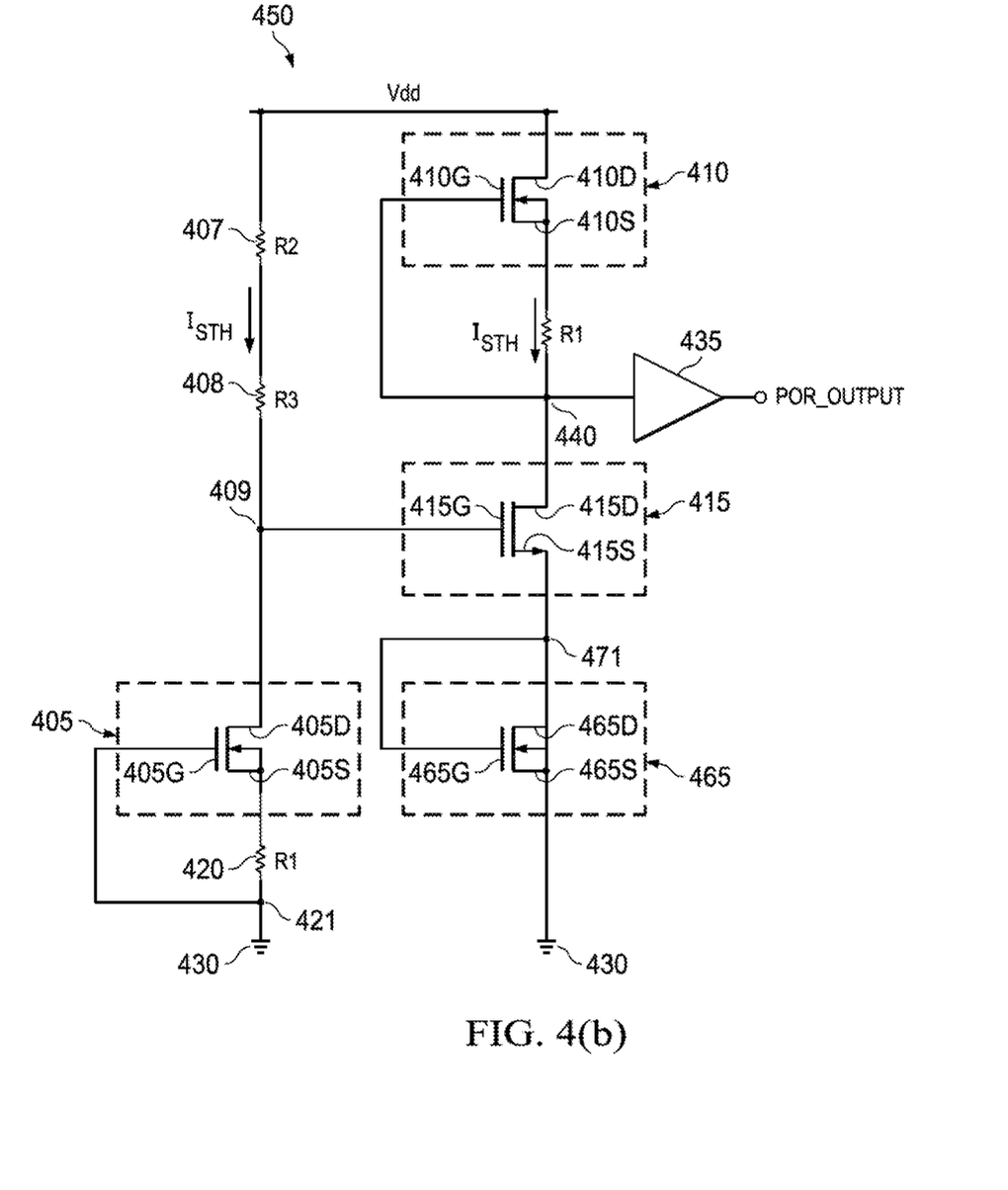
FIG. 4(b) depicts a schematic diagram of yet another illustrative POR circuit, in accordance with an example.

FIG. 4(*b*) depicts the POR circuit 450. The POR circuit 450 is similar to the POR circuit 400 except for an additional transistor 465 and resistor 408. The resistor 408 has a resistance R3 and is coupled to the resistor 407 and to the node 409. The transistor 465 has a source terminal 465*s*, a drain terminal 465*d*, and a gate terminal 465*g*, where the gate terminal 465*g* is coupled to the drain terminal 465*d* at a node 471, which is further coupled to the source terminal 415*s*. The source terminal 465*s* couples to the ground node 430. In some examples, the transistor 465 may be an NFET having the low threshold voltage between 0.5 V–0.6 V. The description of the POR circuit 400 applies to the description of the POR circuit 450. Due to the additional transistor and resistor, the POR circuit 450 assumes a 3-transistor, 3-resistor (3T-3R) architecture relative to the 2T-2R architecture of the POR circuit 400.

In the POR circuit 450 operation, the voltage at the node 409 in the POR circuit 450 is equal to the difference of the supply voltage Vdd and the voltage drop across the resistors 407, 408 ($V_{409}$=Vdd−$I_{STH}$*(R2+R3)). As the supply voltage Vdd increases from zero to some finite value, e.g., 0.3V, a current $I_{STH}$ starts flowing due to the transistors 405. The current $I_{STH}$ flows into the resistors R2, R3. At this point, the voltage at the node 409 starts increasing from zero to a voltage equaling 0.3−($I_{STH}$*R2). Because the voltage on the node 409 is less than the threshold voltage of the transistor 415 (which, in this example, is 0.7V), the transistor 415 remains in an OFF state, and the voltage at the node 440 is forced to be equal to the supply voltage Vdd. At this point, the POR outputs a logic high (e.g., 1) signal indicating that the supply voltage has not reached the desired voltage level (which, in this example, is the sum of the threshold voltage of the transistors 415 and 465, and the voltage drop across resistors R2 and R3). When the supply voltage Vdd approaches a voltage value equaling the sum of the threshold voltage of the transistors 415 and 465, and the voltage drop across resistors R2 and R3, the transistor 415 begins to turn ON and the voltage at the node 440 begins to fall below the supply voltage Vdd. When the supply voltage Vdd crosses a voltage value equaling the sum of the threshold voltage of the transistors 415 and 465, and the voltage drop across resistors R2 and R3, the transistor 415 turns ON, which, in turn, forces the voltage on node 440 to be at a low voltage (e.g., 10 mV+$V_{gate\text{-}to\text{-}source\_465}$) with transistor 415 operating in a deep triode region. The transistor 465 has a low threshold voltage and is operating in the subthreshold region. This introduces a low value of $V_{gate\text{-}to\text{-}source\_465}$ (e.g., 0.4-0.5V). The voltage on node 440 is thus logic low concerning the input of buffer 435, signifying that the supply voltage has reached the desired level.

Similar to the POR circuits 200, 300, and 400, a trip voltage ($V_{TRIP+}$) for the POR circuit 450 is computed by equation 11:

$$V_{TRIP+} \cong V_{th\_415} - V_{th\_410} - V_{th\_420} + V_{th\_465} + mV_T \ln\left(\frac{\beta_{410}\beta_{405}}{\beta_{465}\beta_{415}}\right) \quad (11)$$

where $\beta_{410}$, $\beta_{415}$ and $\beta_{465}$ are equal to $$\mu * C_{ox} * \frac{W}{L}$$

of the transistors 410, 415, and 465 respectively; m is subthreshold slope factor of the transistors 410, 415, and 465; $V_{th\_415}$ is the threshold voltage of the transistor 415; $V_{th\_410}$ is the threshold voltage of the transistor 410; and $V_{th\_415}$ is the threshold voltage of the transistor 465. By comparing the trip voltages of the POR circuits 400, 450, the transistor 465 increases the trip point of the POR circuit 450.

In this description, an element or feature that is "configured to" perform a task or function may be configured (e.g., programmed or structurally designed) at a time of manufacturing by a manufacturer to perform the function and/or may be configurable (or reconfigurable) by a user after manufacturing to perform the function and/or other additional or alternative functions. The configuring may be through firmware and/or software programming of the device, through a construction and/or layout of hardware components and interconnections of the device, or a combination thereof Also, in this description, the term "ground" or similar phrase includes a chassis ground, an Earth ground, a floating ground, a virtual ground, a digital ground, a common ground, and/or any other form of ground connection applicable to, or suitable for, the teachings of this description. Unless otherwise stated, in this description, "about," "approximately" or "substantially" preceding a value means +/−10 percent of the stated value.

Modifications are possible in the described examples, and other implementations are possible, within the scope of the claims.

What is claimed is:
1. A power-on reset (POR) circuit comprising:
   first, second and third resistors;
   a first transistor having a first control terminal and first and second voltage terminals, the first control terminal coupled via the first resistor to the second voltage terminal;
   a second transistor having a second control terminal and third and fourth voltage terminals, the third voltage terminal coupled via the second resistor to the first voltage terminal, and the second control terminal coupled via the third resistor to the fourth voltage terminal;
   a third transistor having a third control terminal and fifth and sixth voltage terminals, the third control terminal coupled to the third voltage terminal, and the fifth voltage terminal coupled to the first control terminal; and
   a voltage buffer coupled to the fifth voltage terminal.
2. The POR circuit of claim 1, wherein the sixth voltage terminal is coupled to a ground terminal.
3. The POR circuit of claim 2, further comprising a fourth transistor coupled between the sixth voltage terminal and the ground terminal.
4. The POR circuit of claim 3, wherein the first voltage terminal is coupled to a voltage source terminal.

5. The POR circuit of claim 2, wherein the first voltage terminal is coupled to a voltage source terminal.

\* \* \* \* \*